Figure 1:
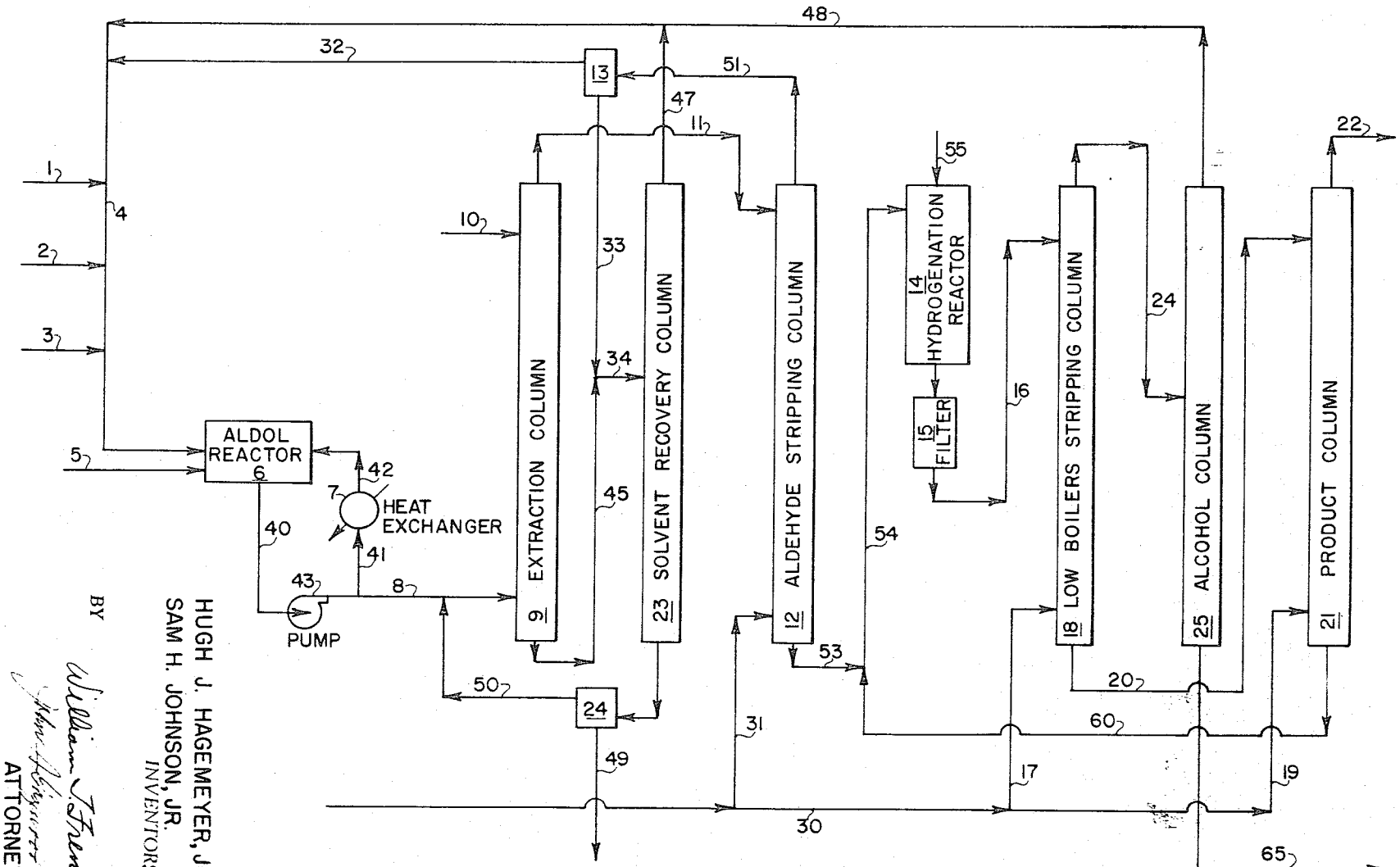

DEFENSIVE PUBLICATION

UNITED STATES PATENT OFFICE

Published at the request of the applicant or owner in accordance with the Notice of Dec. 16, 1969, 869 O.G. 687. The abstracts of Defensive Publication applications are identified by distinctly numbered series and are arranged chronologically. The heading of each abstract indicates the number of pages of specification, including claims and sheets of drawings contained in the application as originally filed. The files of these applications are available to the public for inspection and reproduction may be purchased for 30 cents a sheet.

Defensive Publication applications have not been examined as to the merits of alleged invention. The Patent Office makes no assertion as to the novelty of the disclosed subject matter.

PUBLISHED NOVEMBER 30, 1971

892 O.G. 1605

T892,025

PROCESS FOR PREPARATION OF 2,2-DIALKYL-PROPANE-1,3-DIOL

Hugh J. Hagemeyer, Jr., and Sam H. Johnson, Jr., both of Box 2068, Longview, Tex. 75601

Continuation of application Ser. No. 732,165, May 27, 1968. This application Aug. 24, 1970, Ser. No. 66,638

Int. Cl. C07c *31/02, 47/02*

U.S. Cl. 260—635 P

1 Sheet Drawing. 15 Pages Specification

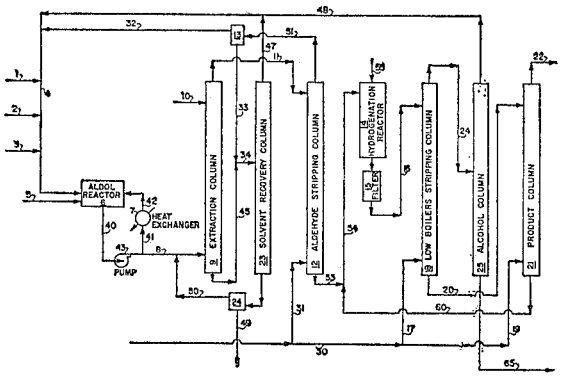

A process for preparing 2,2-dialkylpropane-1,3-diols by contacting an alcoholic solution of an aldehyde having a single alpha-hydrogen atom and from 5 to 23 carbon atoms with formaldehyde in the presence of a caustic aldol condensation catalyst. The aldehyde is present in a ratio of from 1 to 3 moles of aldehyde per mole of formaldehyde. The reaction is conducted at a temperature of from 0° C. to 40° C. to form an aldol. The alcohol, salts and catalyst residue are removed by water washing. Other dissolved impurities and unreacted reagents are removed by stripping with a heated inert gas. The purified aldol is reduced with hydrogen in the presence of a barium-promoted copper-chromium oxide catalyst and subsequently stripped of reduction by-products with an inert gas to yield the essentially pure diol.

Nov. 30, 1971 H. J. HAGEMEYER, JR., ET AL T892,025

PROCESS FOR PREPARATION OF 2,2-DIALKYLPROPANE-1,3-DIOL

Original Filed May 27, 1968

HUGH J. HAGEMEYER, JR.
SAM H. JOHNSON, JR.
INVENTORS

BY William T. French
John A. Bigwood
ATTORNEYS